(12) United States Patent
Chueh

(10) Patent No.: US 6,346,408 B1
(45) Date of Patent: Feb. 12, 2002

(54) METHOD OF ALLOPHYCOCYANIN INHIBITION OF ENTEROVIRUS AND INFLUENZA VIRUS REPRODUCTION RESULTING IN CYTOPATHIC EFFECT

(76) Inventor: Chuang-Chun Chueh, P.O. Box No. 6-57, Chung Ho City, Taipei Hsien 235 (TW)

( * ) Notice: Subject to any disclaimer, the term of this patent is extended or adjusted under 35 U.S.C. 154(b) by 0 days.

(21) Appl. No.: 09/698,111

(22) Filed: Oct. 30, 2000

(30) Foreign Application Priority Data

Jul. 6, 2000 (TW) .......................................... 89111092

(51) Int. Cl.[7] ................................................ C12N 5/00

(52) U.S. Cl. .................. 435/238; 424/780; 424/195.17; 436/531; 435/236; 422/28

(58) Field of Search ............................. 435/4, 8, 5, 188, 435/7.92, 961, 962, 235.1, 238, 236; 436/531; 514/514, 516; 424/780, 195.17; 422/28

(56) References Cited

U.S. PATENT DOCUMENTS 4,898,891 A * 2/1990 Lavie et al.

* cited by examiner

*Primary Examiner*—Leon B. Lankford, Jr.
*Assistant Examiner*—Ruth A. Davis
(74) *Attorney, Agent, or Firm*—Troxell Law Offices PLLC

(57) ABSTRACT

A method of allophycocyanin inhibition of enterovirus and influenza virus reproduction resulting in cytopathic effect, with the ingredients utilized including allophycocyanin, wherein a virus and cell culture is first cultivated in an incubator containing a culture medium solution and following cell preparation, the virus suspension of the preparation is quantitatively determined and an antiviral pharmaceutical inhibition concentration determination procedure is utilized for pharmaceutical neutralization experiments, the results indicating that allophycocyanin possesses enterovirus neutralization capability; furthermore, utilizing ingredients including allophycocyanin as the primary ingredient, virus and cells are first cultivated in an incubator containing a culture medium solution and following a virus plaque inhibition assay, the results indicate that allophycocyanin possesses influenza virus reproduction inhibition capability.

8 Claims, 3 Drawing Sheets

US 6,346,408 B1

METHOD OF ALLOPHYCOCYANIN INHIBITION OF ENTEROVIRUS AND INFLUENZA VIRUS REPRODUCTION RESULTING IN CYTOPATHIC EFFECT

BACKGROUND OF THE INVENTION

1) Field of the Invention

The invention herein relates to a method of allophycocyanin inhibition of enterovirus and influenza virus reproduction to prevent cytopathic effect, specifically referring to a method that utilizes allophycocyanin as a primary ingredient and wherein the results of pharmaceutical neutralization experiments as well as virus plaque assays verify a technique of inhibiting enterovirus and influenza reproduction to prevent cytopathic effect.

2) Description of the Prior Art

Viruses are the cause of various human diseases such as hepatitis, influenza, digestive tract pathology, auto-immune deficiency syndrome, and certain cancers, with the current preventive and treatment methods including vaccines and antivirotics; of these, vaccines had the earliest observable effectiveness, but at present no breakthroughs whatsoever in antivirotics have been noted.

According to relevant documentary reports, antiviral activity inhibits the multiplying of virus in host cells but at the same also inhibits cell function and is manifested as cell toxicity. Following antiviral pharmaceutical development, the antiviral medicinal properties situation has become more and more serious; clinically, viral drug-resistance often occurs with patients lacking full immune functions because under such conditions virus proliferate in substantial quantities and pharmaceutical contact periods increase, thereby giving rise to drug-resistant cytopathogenic mutant strains of virus that have the opportunity to successfully survive such that pharmaceutical effects are lost; based on relevant documents, when antiviral substances are selectively reviewed and antiviral active substance items generally evaluated, although there is extensive research concerning natural antiviral substances and chemical-based antiviral substances in viral inhibiting applications as well as the inhibition of antiviral cytopathogenic mutant strains, no reports whatsoever have been seen about the techniques of allophycocyanin inhibition of enterovirus or allophycocyanin inhibition of influenza virus.

MEANS OF SOLVING THE PROBLEM

The invention herein utilizes allophycocyanin as an antiviral substance, wherein this biological pigment is added in a method to inhibit enterovirus reproduction as well as influenza virus reproduction to prevent cytopathic effect.

The brief description of the drawings below are followed by the detailed description of the invention which elaborates the related formulation and experimental procedures.

DETAILED DESCRIPTION OF THE INVENTION

I. Method of Allophycocyanin Inhibition of Enterovirus Reproduction Resulting in Cytopathic Effect A. The method of allophycocyanin inhibition of enterovirus reproduction resulting in cytopathic effect utilizes the following ingredients:

A reference virus:
Enterovirus 71 prototype BrCr.
Cells:
Human embryonal rhabdomyosarcoma (RD) cells.
Reference compounds:
Allophycocyanin.
5% glutaraldehyde.
0.1% crystal violet: After fully dissolving 2 gm of crystal violet in 100% alcohol, the solution is screened through a 0.45 µm filter and two liters of water are added as a diluent.

Utilizing the said ingredients, the virus and cells are first cultivated in an incubator containing the culture medium solution and following cell preparation, the virus suspension of the preparation is quantitatively determined and an antiviral pharmaceutical inhibition concentration determination procedure is utilized for pharmaceutical neutralization experiments, the results indicating that allophycocyanin possesses enterovirus 71 neutralization capability.

Figure 1:
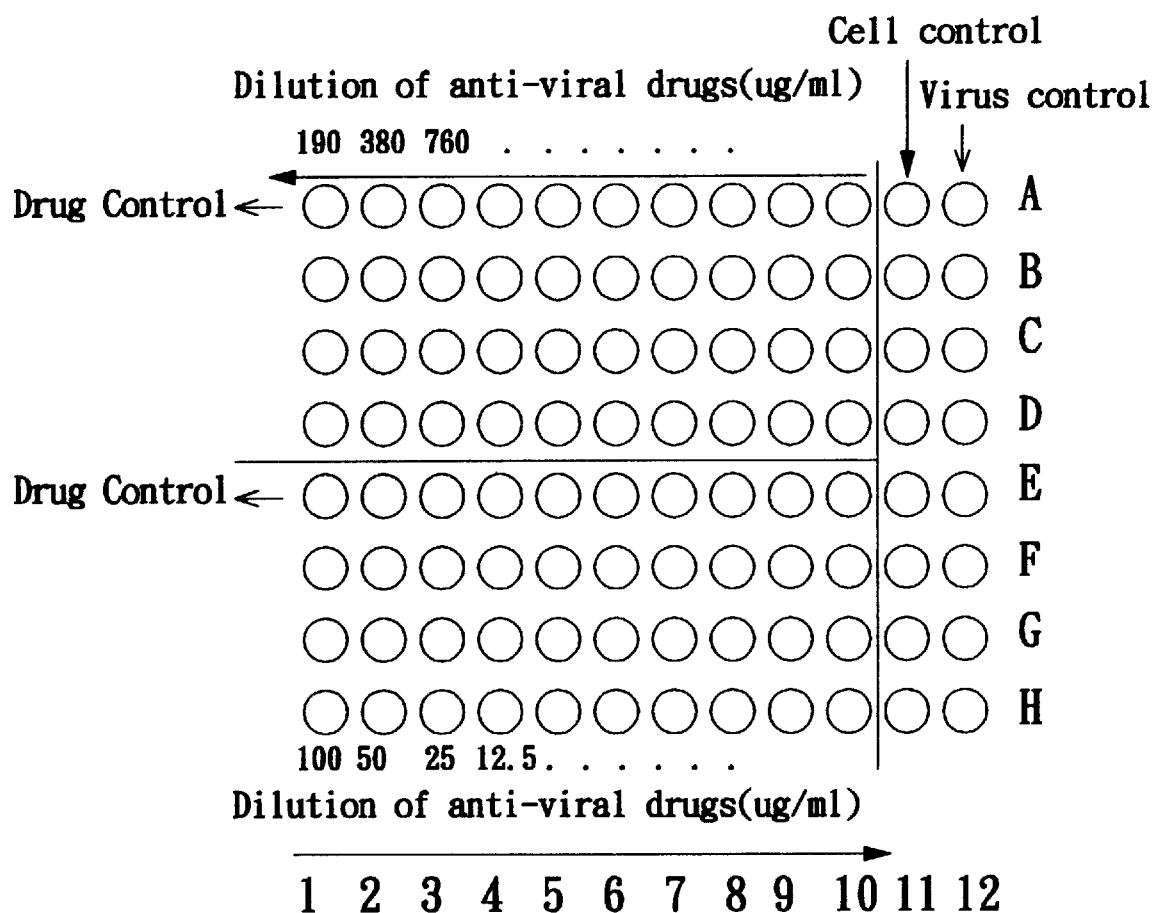
FIG. 1 is a diagram of the antiviral pharmaceutical inhibition concentration determination method of the invention herein.
Figure 2:
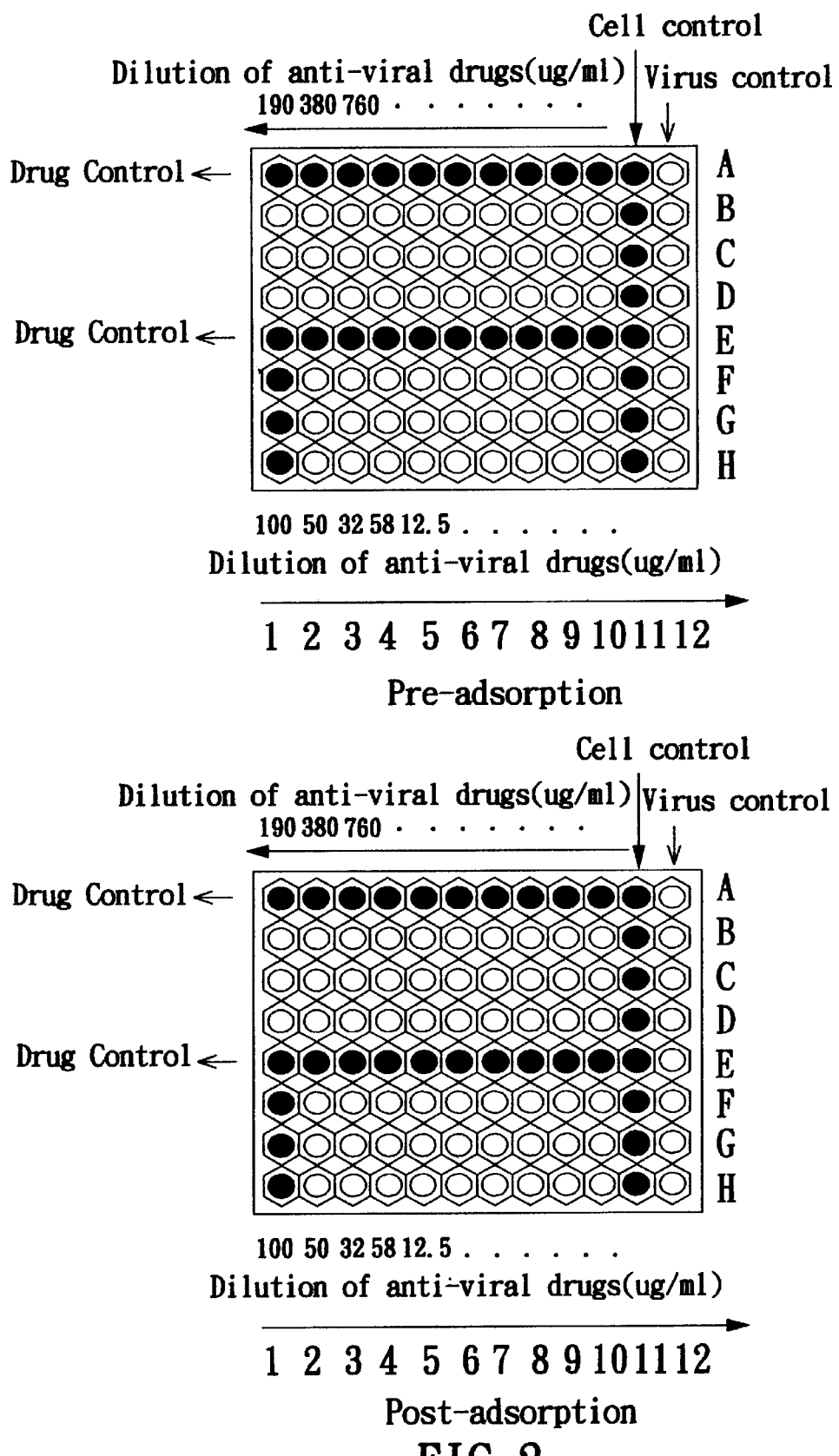
FIG. 2 is a drawing of the allophycocyanin neutralized enterovirus culture plate.
Figure 3:
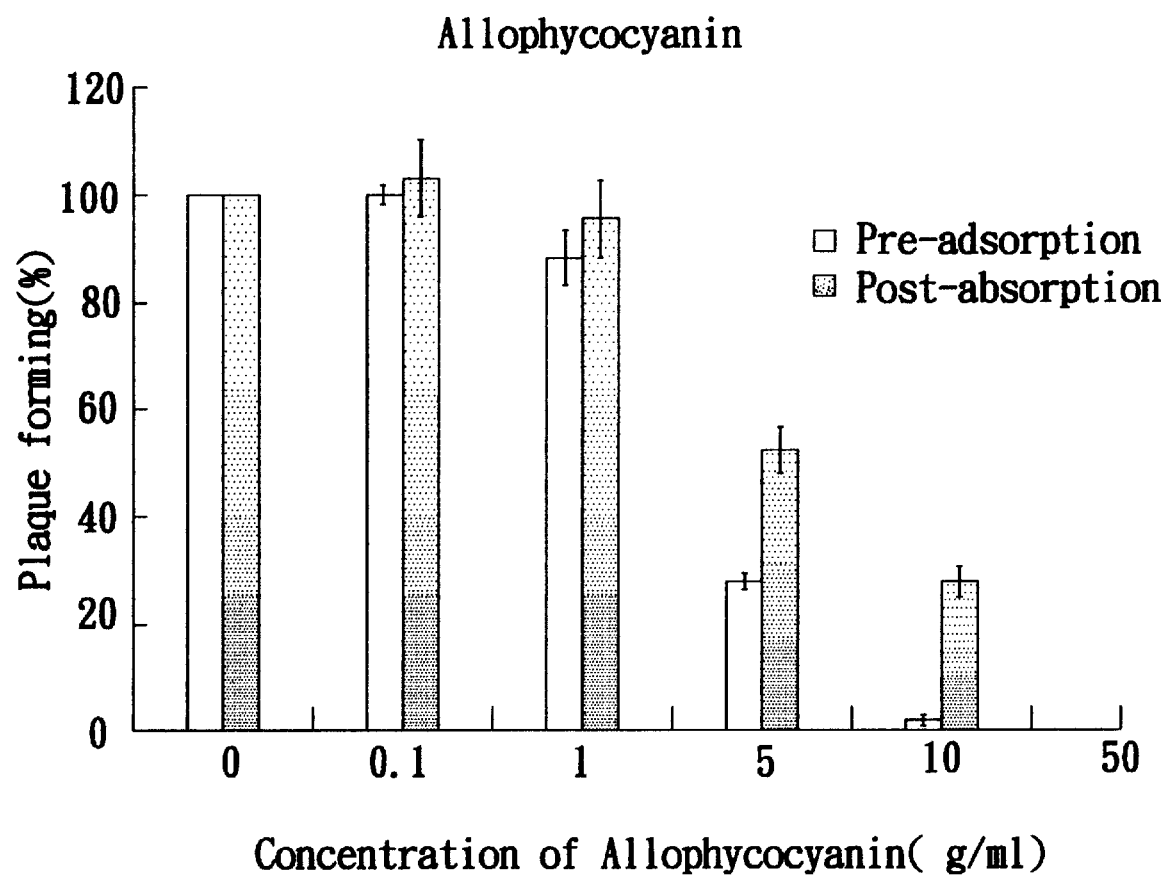
FIG. 3 is an assay chart of the allophycocyanin inhibition of influenza virus reproduction.

B. Allophycocyanin Enterovirus 71 Inhibition Capability Allophycocyanin:

Neutralized enterovirus 71 type, IC50=50 µg/ml, as indicated in FIG. 2.

Through the said virus and cell culture method, pharmaceutical neutralization experiments and the results of the said experiments are assessed to verify that the allophycocyanin demonstrably neutralizes enterovirus type 71 and has enterovirus type 71 inhibition capability.

II. Method of Allophycocyanin Inhibition of Influenza Virus Reproduction

The method of allophycocyanin inhibition of influenza virus reproduction similarly utilizes allophycocyanin as a primary ingredient and following virus and cell culturing as well as a final virus plaque inhibit assay, the results confirm that allophycocyanin possesses influenza virus reproduction inhibition capability.

What is claimed is:

1. A method for inhibiting viral reproduction comprising:
   cultivating a virus and cell culture in an incubator containing a culture medium solution, said virus being an enterovirus or an influenza virus;
   determining quantitatively said virus in suspension in said cell preparation;
   determining a concentration of allophycocyanin sufficient to inhibit said virus in suspension; and
   inhibiting reproduction of said virus with said concentration of allophycocyanin to prevent cytopathic effects.

2. A method for inhibiting viral reproduction, wherein said virus is an enterovirus or an influenza virus, comprising:
   preparing a reference virus of enterovirus 71 prototype BrCr in a culture of human embryonal rhabdomyosarcoma (RD) cells;
   preparing a reference compound, said reference compound including:
   allophycocyanin;
   5 percent glutaraldehyde; and
   0.1 percent crystal violet, wherein a solution is formed after 2 grams of crystal violet are fully dissolved in 100 percent alcohol, said solution is screened through a 0.45 µm filter, and two liters of water are added as a diluent;
   cultivating said reference virus and said cell culture in an incubator containing a culture medium solution;
   determining quantitatively said reference virus in suspension;

determining a concentration of allophycocyanin sufficient to inhibit said reference virus in suspension; and inhibiting reproduction of said reference virus with said concentration of allophycocyanin.

3. The method of claim 2 wherein the step of cultivating further comprises:

cultivating said rhabdomyosarcoma (RD) cells in a culture medium solution consisting of:
10 percent fetal bovine serum;
0.026 sodium bicarbonate;
100 units/ml penicillin; and
100 µg/ml amphotericin-B of Dulbecco's Modified Eagle Medium (DMEM) at pH 7.4 within an incubator containing 5 percent $CO_2$ and operating at a temperature of 37° C. such that, during said cultivating, said cells are first immersed twice in a 1 phosphate buffer saline (PBS) solution and an appropriate volume of trypsin is added to process said cells and to facilitate removal of said cells from culture plate surfaces;

stopping reaction of said trypsin with an appropriate amount of culturing solution;

centrifuging for three minutes at a speed of 1,000 rpm;

removing clear liquid by a pipet;

resuspending said cells in a fresh solution of said culturing solution; and placing said cells in a culture plate for continued cultivating.

4. The method of claim 2 wherein said step of determining a concentration of allophycocyanin sufficient to inhibit said virus further comprises:

(A) depositing 200 µl of the said rhabdomyosarcoma (RD) cells in units of 3×10 cells/ml on a 96-well culture plate and cultivating at a temperature of 37° C. for 24 hours within an incubator containing 5 percent $CO_2$ to grow a complete single layer of cells;

(B) performing a virus suspension quantitative determination including:

(1) preparing a dilute virus solution in a 96-well culture plate with 171 µl containing 2 percent PBS of DMEM added into said wells of column 1 at A1 to H1 and, after adding 79 µl of virus solution, mix equally; 79 µl of virus solution is added into said wells of column 2, then from 2, 79 µl are added to 3 to provide a 0.5 log series dilution up to column 10 with $10^{0.5}$ to $10^5$ dilution, in octuplicate;

(2) removing with said pipette said media from the 96-well culture plate and adding said media into the 150 µl virus dilution of step B(1), then place for one hour in an incubator operating at a temperature of 37° C. and containing 5 percent $CO_2$ to allow the virus adsorption into the cells;

(3) adding, after one hour of adsorption, the 50 µl solution of 2 percent PBS of DMEM and cultivate for two days in an incubator operating at a temperature of 37° C. and containing 5 percent $CO_2$; and (4) performing a virus quantitative determination, after said two days, by adding 100 µl of the 5 percent glutaraldehyde to congeal for one hour at room temperature, dye with 0.1 percent crystal violet for 15 minutes and then rinse in tap water and measure the $OD_{570}$, whereby the virus titer is the highest dilution concentration, being less than 15 percent of the control $OD_{570}$, of more than 85 percent CPE as produced by a total of eight wells.

5. The method of claim 2 wherein said step of determining said concentration of allophycocyanin sufficient to inhibit said virus at an ID50 at 50 percent inhibition dose further comprises:

(1) depositing 200 µl of the said rhabdomyosarcoma (RD) cells in units of 3×10 cells/ml on a 96-well culture plate and cultivating at a temperature of 37° C. for 24 hours within an incubator containing 5 percent $CO_2$ to grow a complete single layer of cells;

(2) preparing a virus solution of a 2 percent PBS of DMEM that reduces virus concentration by dilution to the concentration of a virus titer that is the highest dilution concentration, being less than 15 percent of the control $OD_{570}$, of more than 85 percent CPE as produced by a total of eight wells;

(3) utilizing a DMEM free of blood serum for series dilution from 100 µg/ml to 190 µg/ml with a PC from 50 µg/ml to 95 µg/ml;

(4) utilizing 150 µl of diluted virus solution with column 11 at A1 to A10 and E1 to E10 containing 2 percent PBS of DMEM to serve as a control group and simultaneously adding 50 µl of diluted allophycocyanin to one group and adding 50 µl of diluted allophycocyanin to the other group one hour after virus adsorption; and (5) cultivating for two days at a temperature of 37° C. for 24 hours within an incubator containing 5 percent $CO_2$.

6. The method of claim 2 further comprising: assessing said inhibiting of reproduction of said virus by said concentration of allophycocyanin as follows:

(1) concentration of allophycocyanin neutralization (+) of Virus: CPE (−), crystal violet (+);

(2) concentration of allophycocyanin IC50=[(Y-B)/(A-B)]×(H-L)+L wherein,
Y is the mean OD570 of said control cell wells (A11 to H11)/2;
B is the mean OD570 of the allophycocyanin dilution well that is less than Y;
A is the mean OD570 of the allophycocyanin dilution well that is more than Y;
L is the concentration of allophycocyanin at B; and
H is the concentration of allophycocyanin at A.

7. The method of claim 1 wherein the virus and cell culture comprises:

cultivating canine kidney cortex cells of an MDCK culture cell reference in a culture medium solution containing 10 percent fetal bovine serum/PBS, 0.026 sodium bicarbonate, 100 units/ml penicillin, 100 µg/ml streptomycin, 0.25 µg/ml amphotericin-B of Dulbecco's Modified Eagle Medium (DMEM) at pH 7.4 within an incubator containing 5 percent $CO_2$ and operating at a temperature of 37° C. such that, during said cultivating, said cells are first immersed twice in a 1×phosphate buffer saline (PBS) solution and an appropriate volume of trypsin is added to process said cells and to facilitate removal of said cells from culture plate surfaces;

stopping reaction of said trypsin with an appropriate amount of culture solution;

centrifuging for three minutes at a speed of 1,000 rpm;

removing clear liquid by a pipet;

resuspending said cells in a fresh solution of said culturing solution; and placing said cells in a culture plate for continued cultivating.

8. The method of claim 1 wherein said inhibiting reproduction of said virus with said concentration of allophycocyanin further comprises:

depositing MDCK cells in a 96-well culture plate wherein each well contains 5×10 cells;

cultivating said cells at a temperature of 37° C. within an incubator containing 5 percent $CO_2$ to grow a complete single layer of cells;

placing said concentration of allophycocyanin in a culture solution of 2 percent fetal bovine diluted ten times in series;

ascertaining an approximate effective antiviral period during a virus plaque assay as follows:

adding said concentration of allophycocyanin to one group of said cells during said virus adsorption and another group after virus adsorption;

placing in each well 100 PPU of virus suspension solution at 0.5 ml/well and cultivating for one hour at a temperature of 37° C. in an incubator with the culture plate being agitated once every 15 minutes to equally distribute said virus;

removing with a pipet, after completion of adsorption, said virus suspension solution and adding said virus solution into a culture solution consisting of a different concentration of allophycocyanin and 0.3 percent agarose and, following stationary solidification, cultivating for two days at a temperature of 37° C. within an incubator containing 5 percent $CO_2$;

adding, after said two days of cultivating, 2 ml of 10 percent formalin into each well and permitting said culture to stand at room temperature for one to two hours; and turning over the congealed membrane and applying 1 percent crystal violet for two minutes and then rinsing with tap water and counting whereby the results of the virus plaque inhibit assay indicate that allophycocyanin inhibits reproduction of enterovirus and influenza virus.

* * * * *